(12) United States Patent
Takada et al.

(10) Patent No.: US 6,649,590 B2
(45) Date of Patent: *Nov. 18, 2003

(54) METHOD OF PRODUCING FRACTIONS CONTAINING A HIGH CONCENTRATION OF MILK BASIC CYSTATIN AND DECOMPOSITION PRODUCTS THEREOF

(75) Inventors: Yukihiro Takada, Kawagoe (JP); Atsushi Serizawa, Kawagoe (JP); Yasuhiro Matsuoka, Kiyose (JP); Yasuhiro Toba, Musashino (JP); Hiroshi Kawakami, Kawagoe (JP)

(73) Assignee: Snow Brand Milk Products Co., Ltd., Hokkai-do (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/876,267

(22) Filed: Jun. 6, 2001

(65) Prior Publication Data

US 2003/0013661 A1 Jan. 16, 2003

(30) Foreign Application Priority Data

Jun. 9, 2000 (JP) .......................... 2000-172852
Jun. 20, 2000 (JP) .......................... 2000-184349

(51) Int. Cl.$^7$ .................. A61K 38/00; A01N 37/18; A23C 1/00
(52) U.S. Cl. ................ 514/2; 514/773; 514/775; 426/491; 426/271; 426/587; 426/588; 426/590; 426/41; 426/42; 426/656; 426/657; 426/2
(58) Field of Search .......................... 426/491, 2, 271, 426/587, 588, 590, 41, 42, 656, 657; 514/773, 2, 775

(56) References Cited

U.S. PATENT DOCUMENTS 5,932,259 A * 8/1999 Kato et al. .................. 426/42
5,976,597 A * 11/1999 Takada et al. .............. 426/491

FOREIGN PATENT DOCUMENTS

| JP | 4-183371 | 6/1992 |
| JP | 5-176715 | 7/1993 |
| JP | 5-320066 | 12/1993 |
| JP | 2000-281587 | 10/2000 |

OTHER PUBLICATIONS

Bruce D. Korant, et al., Cystatin, A Protein Inhibitor Of Cysteine Proteases Alters Viral Protein Cleavages In Infected Human Cells, Biochemical and Biophysical Research Communications Vo. 127, No. 3, Mar. 29, 2995, pp. 1072–1076.

* cited by examiner

Primary Examiner—Christopher S. F. Low
Assistant Examiner—Chih-Min Kam
(74) Attorney, Agent, or Firm—Knobbe, Martens Olson & Bear LLP

(57) ABSTRACT

A milk basic protein fraction is heated if necessary, the resulting precipitate is removed to recover the resulting supernatant, alcohol is added to this supernatant, a fraction containing a high concentration of milk basic cystatin is recovered by removing the resulting precipitate and brought into contact with a carrier containing a sulfuric acid group, such as heparin, to recover a fraction which is not adsorbed onto the carrier, and this fraction is then treated with an ultrafiltration membrane having an cut-off molecular weight of 10–50 kDa to recover the permeate to produce a fraction containing a high concentration of milk basic cystatin. Alternatively, a milk-derived basic protein composition is brought into contact with an anion exchange resin to recover a fraction which is not adsorbed onto the resin, after which this fraction is brought into contact with a cation exchange resin to recover the target fraction by eluting a fraction which is adsorbed onto the resin with an eluent to produce a fraction containing a high concentration of milk basic cystatin. Further, a decomposition product of the fraction containing a high concentration of milk basic cystatin is produced by decomposing this fraction containing a high concentration of milk basic cystatin with protease.

27 Claims, No Drawings

METHOD OF PRODUCING FRACTIONS CONTAINING A HIGH CONCENTRATION OF MILK BASIC CYSTATIN AND DECOMPOSITION PRODUCTS THEREOF

BACKGROUND OF THE INVENTION

1. Field of the Invention

The present invention relates to a method of producing a fraction containing a high concentration of milk-derived basic cystatin from a milk-derived basic protein fraction.

The present invention also relates to a method of producing a decomposition product of the resulting fraction containing a high concentration of milk-derived basic cystatin by decomposing said fraction containing a high concentration of milk-derived basic cystatin using a protease.

Further, the present invention relates to a drink, food product, medicine and feed to which the fraction containing a high concentration of milk-derived basic cystatin and/or the decomposition product of the fraction containing a high concentration of milk-derived basic cystatin milk-derived basic cystatin are admixed, and if necessary, calcium and/or vitamins are additionally admixed, for the prevention and treatment of various bone diseases such as osteoporosis, bone joint diseases such as rheumatism, and periodontal disease.

2. Description of the Related Art

In recent years, the number of people suffering from various bone diseases, such as bone fractures and lumbago has been on the rise because of the aging population. Bone formation and bone resorption continuously take place in bone tissue and are well balanced in early life, but the balance is lost with an increase in bone resorption with aging for various reasons. If this unbalance continues for a long period of time, the bone tissue becomes fragile, which results in various bone diseases such as osteoporosis, bone fractures and lumbago. It is believed that if this uncoupling leaning toward bone resorption can be impeded, various bone diseases can be prevented.

Conventional methods to prevent and treat various bone diseases include (1) dietary supplementation of calcium, (2) moderate exercise, (3) sunbathing, and (4) administration of medicines. For dietary supplementation, calcium salts such as calcium carbonate and calcium phosphate, natural calcium supplements such as bovine bone powders, eggshells and fish bone powders are used. For moderate exercise, moderate running or walking are highly recommended. However, even moderate exercise is difficult for people who are physically weak and, not to mention, almost impossible for elderly people who are confined to bed. The third method, sunbathing, is good for the supplementation of activated vitamin $D_3$, but not sufficient by itself. For the last method, administration of medicines, 1α-hydroxy vitamin $D_3$, calcitonin preparations or the like are known to be effective to cure and treat osteoporosis. It is believed that bone joint diseases, such as rheumatism, and periodontal disease can be treated by suppressing bone resorption since they are ultimately associated with the bone resorption.

The present inventors intensively searched for a milk whey protein fraction having an osteoblast growth stimulating factor, a bone resorption suppressing factor and bone strengthening activity, in order to obtain a material which is effective for the prevention and treatment of various bone diseases, bone joint diseases and periodontal disease. Namely, the present inventors fractionated proteins in milk, in particular milk whey, in an attempt to obtain a fraction having a suppressing activity on osteoclastic bone resorption. As a result, the present inventors found that a bone strengthening activity in a protein-peptide mixture which was obtained by treating a water soluble fraction of whey proteins with a reverse osmotic membrane or electrodialysis to remove salts (Japanese Patent Application Laid-open No. H4-183371). Furthermore, the present inventors found that a fraction obtained by treating an aqueous solution of this protein-peptide mixture with ethanol, heat, salts or an ultrafiltration membrane has a bone strengthening activity (Japanese Patent Application Laid-open No. H5-176715, Japanese Patent Application Laid-open No. H5-320066). The present inventors also found that basic proteins present in milk in trace amounts have a collagen synthesis stimulating activity in osteoblasts and bone resorption preventing activity (Japanese Patent Application Laid-open No. H7-207509).

Cystatin, a cysteine protease inhibitor, is a substance which inhibits proteolytic activity of cysteine proteases having an SH group in the active center and is found in animal tissues, cells, blood and urine. Further, a virus growth inhibiting activity is recognized as a useful activity of cystatin (Biochem. Biophys. Res. Commun., Vol. 127, p. 1072, 1985).

In recent years, the number of people suffering from osteoporosis caused by osteoclastic bone resorption has been rapidly increasing. Currently, a calcitonin drug is known as a medicine to suppress this osteoclastic bone resorption. However, a calcitonin drug is a hormonal agent used as a medicine, and the safety of its use as a food material has not been examined to this day. Further, production of calcitonin in bulk from animal tissues, cells, blood or urine for use as a food material has not been attained.

SUMMARY OF THE INVENTION

The present inventors tried to isolate and purify an active substance having a bone resorption suppressing activity from a basic protein fraction having a bone resorption suppressing activity, identified the resulting isolated and purified substance, and confirmed that this substance is a milk basic cystatin. Furthermore, the present inventors found that the milk basic cystatin has a suppressing activity more specifically on osteoclastic bone resorption, as compared with other kinds or types of cystatins from origins other than milk (Japanese Patent Laid-open No. 2000-281587, published Oct. 10, 2000, which is after the priority date of this application).

Under these circumstances, a method of producing a milk-derived basic cystatin usable as a food material in bulk and at a low cost is in need. Accordingly, an object of the present invention is to provide a method of producing a fraction containing a high concentration of basic cystatin from a milk-derived basic protein fraction.

Further, an object of the present invention is to provide a method of producing a decomposition product of the fraction containing a high concentration of milk basic cystatin since a protease decomposition product of the fraction containing a high concentration of milk basic cystatin is also known to have a bone resorption suppressing activity.

Furthermore, another object of the present invention is to provide a drink, food product, medicine or feed to which the fraction containing a high concentration of milk-derived basic cystatin and/or the decomposition product of the fraction containing a high concentration of milk-derived basic cystatin are admixed for the prevention and treatment of various bone diseases such as osteoporosis, bone joint diseases such as rheumatism, and periodontal disease.

The process for extracting basic cystatin from milk is broadly divided into (1) a process to extract a basic protein fraction from milk, and (2) a process to extract basic cystatin from the basic protein fraction. As explained below, a basic protein fraction can be extracted in great volume from milk volume by, for example, contacting milk with a cation exchange resin, and then eluting a fraction adsorbed on the resin with an elute having a salt concentration of 0.1–1.0 M. However, a further treatment is required for recovering basic cystatin at a high concentration such as 1% or higher by dry weight. Separating basic cystatin from other basic proteins can be accomplished to a certain degree by a method utilizing its physico-chemical characteristics, such as steps of heating a solution at 80° or higher, recovering a supernatant by removing the resultant precipitate, adding alcohol to the supernatant, and removing the resultant precipitate. However, it is difficult to obtain basic cystatin at a high concentration by the above method. The present invention provides a method of extracting and recovering basic cystatin at a high concentration from a basic protein fraction. Namely, the present invention is a production method comprising the steps of: (1) preparing a composition containing a milk-derived basic protein fraction; (2) contacting said composition with a carrier containing a sulfuric acid group; (3) recovering a fraction which is not adsorbed onto the carrier; (4) subjecting said fraction to ultrafiltration using a membrane having a cut-off molecular weight of 10–50 kDa; and (5) recovering a permeate from said ultrafiltration membrane to recover a fraction containing milk basic cystatin from said permeate, or a production method comprising the steps of: (1) preparing a milk-derived basic protein composition; (2) contacting said milk-derived basic protein composition with an anion exchange resin; (3) recovering a fraction which is not adsorbed onto said resin; (4) contacting said fraction with a cation exchange resin; and (5) eluting and recovering a fraction which is adsorbed onto said resin with an eluent to recover a fraction containing milk basic cystatin. According to the present invention, a composition of a fraction containing milk basic cystatin containing approximately 1% or higher milk basic cystatin by dry weight can be produced in great volume (preferably, desalting treatment is conducted). In the above, preferably, the obtained fraction is subjected to desalting and concentration treatment such as ultrafiltration (a cut-off molecular weight of 10–50 kDa) or diafiltration.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

DETAILED DESCRIPTION OF THE PREFERRED EMBODIMENT

According to an embodiment of the present invention, a method of producing a fraction containing a high concentration of milk basic cystatin is characterized in that a milk-derived basic protein fraction is heated, if necessary, at 70–90° C. (preferably at 80° C. or higher), the resulting precipitate is removed to recover the supernatant, alcohol is added to this supernatant, at 30–80% preferably at a concentration of 70%), a fraction containing a high concentration of milk basic cystatin is recovered by removing the resulting precipitate. The above processes are not indispensable but useful because the concentration of basic cystatin can be raised to a certain degree. The recovered fraction is then brought into contact with the fraction with a carrier containing a sulfuric acid group (preferably by passing through a column a solution prepared by dissolving the basic protein fraction in a buffer solution having a pH of 4–8 at a final concentration of 1–5% by weight) to recover a fraction which is not adsorbed onto the carrier, and this fraction is then treated with an ultrafiltration membrane having a cut-off molecular weight of 10–50 kDa to recover the permeate. As a carrier containing a sulfuric acid group, a heparin-immobilized column and others.

Further, according to the present invention, a method of producing a decomposition product of the fraction containing a high concentration of milk basic cystatin is characterized in that the fraction containing a high concentration of milk basic cystatin produced by the abovementioned method is further decomposed with a protease.

Further, the present invention is a drink, food product, medicine or feed to which the fraction containing a high concentration of milk-derived basic cystatin and/or the decomposition product of the fraction containing a high concentration of milk-derived basic cystatin are admixed, and if necessary, calcium and/or vitamins are additionally added, for the prevention and treatment of various bone diseases such as osteoporosis, bone joint diseases such as rheumatism, and periodontal disease. The effective dose of a fraction containing milk basic cystatin or its decomposition product may be approximately 1 $\mu$g–100 mg/100 g.

Basic cystatin can also be recovered at a high concentration from a fraction containing milk-derived basic protein by the following method. Namely, according to another embodiment of the present invention, a method of producing a fraction containing a high concentration of milk basic cystatin is characterized in that a milk-derived basic protein composition (preferably, a solution prepared by dissolving a basic protein in a buffer solution having a pH of 4–8 at a final concentration of 1–5% by weight) is brought into contact with an anion exchange resin to recover a fraction which is not adsorbed onto the resin, after which this fraction is brought into contact with a cation exchange resin to recover the target fraction by eluting a fraction which is adsorbed onto the resin with an eluent. As with the previously mentioned method, the recovered fraction is preferably subjected to desalting and concentration treatment.

Milk or a milk product, such as reconstituted milk, skimmed milk, and whey, can be used to obtain a milk-derived basic protein composition, a starting material of the present invention. The milk-derived basic protein composition which is present in milk only in trace amounts comprises primarily lactoferrin and lactoperoxidase. Accordingly the milk-derived basic protein composition can be obtained in bulk by bringing milk into contact with a cation exchange resin, and then eluting a fraction which is adsorbed onto the resin with an eluent having a salt concentration of 0.1–1.0 M.

The eluent to elute the fraction which is adsorbed onto the cation exchange resin can be a solution containing a salt such as 0.1–1.0 M sodium chloride.

Examples of resins to be used in the present invention include commercial Q Sepharose (Pharmacia) as an anion exchange resin and commercial S-Sepharose (Pharmacia) as a cation exchange resin.

The present invention also includes a method of producing a decomposition product of a fraction containing a high concentration of milk basic cystatin by decomposing the fraction containing a high concentration of milk basic cystatin produced by the abovementioned method, with a protease.

Further, the present invention includes a drink, food product, medicine or feed to which the fraction containing a high concentration of milk-derived basic cystatin and/or the decomposition product of the fraction containing a high concentration of milk-derived basic cystatin are admixed, and if necessary, calcium and/or vitamins are additionally added, for the prevention and treatment of various bone diseases such as osteoporosis, bone joint diseases such as rheumatism, and periodontal disease. In the above case (a method using an anion exchange resin and a cation exchange resin in combination), the effective dose of a fraction containing milk basic cystatin or its decomposition product may be approximately 5 $\mu$g–500 mg/100 g, which is slightly higher than in the case of a method using a carrier containing a sulfuric acid group. This is because the purity of basic cystatin in the former is slightly lower than in the latter.

In addition, a method using an anion exchange resin and a cation exchange resin in combination, and a method using a carrier containing a sulfuric acid group can be combined to extract and recover basic cystatin. That is, by conducting one of the methods after conducting the other method, basic cystatin containing can be obtained at a high concentration.

According to the present invention, a safe fraction containing a high concentration of milk basic cystatin can be produced in bulk. Examples of milk to be used include raw milk, powdered milk, powdered skim milk, and reconstituted milk.

Further, a decomposition product of the fraction containing a high concentration of milk basic cystatin of the present invention is a peptide mixture prepared by restrictively decomposing the abovementioned fraction containing a high concentration of milk basic cystatin with a protease, such as trypsin, chymotrypsin, pepsin, papain, kallikrein, cathepsin, thermolysin, and V8 protease. In general, decomposition products exhibit higher activity than the fraction itself. The degree of decomposition of the fraction with an enzyme can be determined with reference to its bone resorption activity.

Further, in the present invention, the abovementioned fraction containing a high concentration of milk basic cystatin and/or decomposition product of the fraction containing a high concentration of milk basic cystatin are added to a drink, food product, medicine or feed. Namely, they can be added to a drink or food product such as milk, milk drinks, juices, jellies, biscuits, breads, noodles, and sausages, made into a form of tablet, powder, tooth paste, or mouthwash for medicinal use, or added to feed.

Further, a highly absorbable calcium is preferably admixed into the drink, food product, medicine and feed of the present invention for the prevention and treatment of various bone diseases such as osteoporosis, bone joint diseases such as rheumatism, and periodontal disease. Examples of the highly absorbable calcium include calcium chloride, calcium carbonate, calcium lactate, eggshells and milk-derived calcium. Vitamins effective for bone formation, such as vitamin D and vitamin K, can also be preferably admixed. A synergistic effect on the bone formation can be attained since these vitamins are different from milk basic cystatin in their actions. Further, milk basic cystatin is an excellent material for food processing because of its high heat stability.

In the present invention, a fraction containing a high concentration of milk basic cystatin and/or decomposition product of the fraction containing a high concentration of milk basic cystatin can be administered in an amount of about 1 $\mu$g to 500 mg (preferably 5 $\mu$g to 100 mg) per day for an adult in divided doses. In this way, various bone diseases such as osteoporosis, bone joint diseases such as rheumatism, and periodontal disease can be prevented and treated.

The present invention will be explained in detail in the following examples.

EXAMPLE 1

A column filled with sulfonated Chitopearl (3,000 g) was thoroughly washed with deionized water. Skimmed milk (10,000 L) was passed through the column, the column was thoroughly washed with deionized water, and then elution was carried out with a linear concentration gradient of 0.1 to 1.0 M sodium chloride. The eluted fraction was freeze-dried to obtain a powder of a milk-derived basic protein fraction. This milk-derived basic protein fraction powder (200 g) was dissolved at a concentration of 1% in an acetic acid buffer solution (pH 5) and the solution was passed through a heparin-immobilized column, manufactured by Pharmacia, and then 20 L of an acetic acid buffer solution (pH 5) was passed through the column to recover 40 L of the passing through fraction. This fraction was concentrated 20 times by treating with an ultrafiltration membrane (cut-off molecular weight: 50 kDa), the resulting permeate was concentrated 10 times by treating with an ultrafiltration membrane (cut-off molecular weight: 10 kDa) to obtain a fraction containing a high concentration of milk basic cystatin. This fraction was freeze-dried to obtain 60 g of a powder fraction containing a high concentration of milk basic cystatin. The milk basic cystatin content of this fraction was 1.8%.

EXAMPLE 2

A column filled with sulfonated Chitopearl (3,000 g) was thoroughly washed with deionized water. Skimmed milk (10,000 L) was passed through the column, the column was thoroughly washed with deionized water, and then elution was carried out with a linear concentration gradient of 0.1 to 1.0 M sodium chloride. The eluted fraction was freeze-dried to obtain a powder form of milk-derived basic protein fraction. This milk-derived basic protein fraction powder (2 kg) was dissolved at a concentration of 5%, the resulting solution was heated at 80C for 15 minutes and then centrifuged to obtain the supernatant. This supernatant (38 kg) was cooled to 5C, ethanol was added at a final concentration of 40%. After maintaining at 5C for 6 hours, the admixture was centrifuged to remove precipitate. Further, ethanol was added to this supernatant at a final concentration of 70%. After maintaining at 5C for 12 hours, the admixture was centrifuged to obtain 240 g of a fraction containing a high concentration of milk basic cystatin (sample A). The milk basic cystatin content of this fraction was 0.7%.

This fraction containing a high concentration of milk basic cystatin (200 g) was dissolved at a concentration of 1% in an acetic acid buffer solution (pH 5), and the solution was passed through a heparin-immobilized column, and then 20 L of an acetic acid buffer solution (pH 5) was passed through the column to recover 40 L of the passing through fraction. This fraction was concentrated 20 times by treating with an ultrafiltration membrane (cut-off molecular weight: 50 kDa), the resulting permeate was concentrated 10 times by treating with an ultrafiltration membrane (cut-off molecular weight: 10 kDa) to obtain a fraction containing a high concentration of milk basic cystatin. This fraction was freeze-dried to obtain 65 g of a powdered fraction containing a high concentration of milk basic cystatin (sample B). The milk basic cystatin content of this fraction was 2.2%.

EXAMPLE 3

The powder fraction containing a high concentration of milk basic cystatin (1 g) obtained in Example 2 was suspended in 100 ml of water, pancreatin was added at a final concentration of 1% by weight, and enzyme treatment was carried out at 37C for 5 hours. Then, the enzyme was inactivated by heating at 90C for 5 minutes, after which 0.91 g of the decomposition product of the fraction containing a high concentration of milk basic cystatin (sample C) was obtained by freeze-drying.

TEST EXAMPLE 1

Splint bones of ICR mice (10–20 days of age) were taken out, soft tissues were removed, then the splint bones were mechanically ground in an α-MEM solution containing 5% fetal calf serum to obtain entire bone marrow cells including osteoclasts. These cells (about $2 \times 10^6$) were spotted on an ivory piece using an α-MEM solution containing 5% fetal calf serum. After several hours, an α-MEM solution containing 5% fetal calf serum, to which each sample was added, was added to the spot, and the ivory piece was incubated for 3 days to examine bone resorption activity of osteoclasts.

After incubation, cells on the ivory piece were pealed, stained with hematoxylin, and subjected to image analysis using PIASLA-555 to count the number of bone resorption pits to evaluate the bone resorption activity.

Thus, a sample solution was each prepared at a concentration of 500 ng/ml for samples A, B and C obtained in Examples 2 and 3 to determine the bone resorption activity. Namely, the bone resorption pits were counted in a culture with an added test sample and compared with the bone resorption pit counts in a culture without an added test sample (referred to as 100%) to express the bone resorption activity. Results are shown in Table 1.

TABLE 1

| Test sample | Bone resorption activity (%, ± SD) |
|---|---|
| Sample A | 81.3 ± 3.9 |
| Sample B | 70.4 ± 5.6 |
| Sample C | 61.5 ± 3.2 |

As shown in Table 1, the fraction containing a high concentration of milk basic cystatin and the decomposition product of the fraction containing a high concentration of milk basic cystatin were revealed to be effective in suppressing bone resorption activity.

However, sample A, which was treated with ethanol, was less effective in suppressing bone resorption activity, than samples B and C which were produced according to a method of the present invention.

TEST EXAMPLE 2

An animal experiment was carried out using osteoporosis model rats for sample B obtained in Example 2 and sample C obtained in Example 3.

Basic ingredients of the feed administered to the rats are shown in Table 2. The amount of both calcium and phosphorus was 300 mg per 100 g feed in all test groups so that the calcium to phosphorus ratio was 1:1.

TABLE 2

| Sucrose | 50.0 |
|---|---|
| | (% by weight) |
| Casein | 20.0 |
| Cornstarch | 15.0 |
| Cellulose | 5.0 |
| Corn oil | 5.0 |
| Vitamin mixture (including choline) | 1.0 |
| Mineral mixture[1] | 4.0 |

[1]Calcium carbonate was admixed as a calcium source.

The following test feeds were prepared by adding sample B or C to the feed with the basic ingredients shown in Table 2. Test feed 1: Feed with the basic ingredients in Table 2+Sample B (0.01 mg/100 g) Test feed 2: Feed with the basic ingredients in Table 2+Sample C (0.01 mg/100 g) Test feed 3: Feed with the basic ingredients in Table 2 (except that milk-derived calcium (Japanese Patent Application Laid-open H4-306622) was used as a calcium source instead of calcium carbonate)+Sample B (0.01 mg/100 g)

Female SD female rats (40 weeks of age) were used for experimental animals. After preliminary rearing for one week, an ovariectomy was performed, and then the rats were reared further for 2 weeks on a low calcium diet to create osteoporosis model rats. Sham operations without an ovariectomy were performed to create sham rats. The rats were divided into groups, 7 rats in one group, and fed the test feeds for one month. The feed with the basic ingredients shown in Table 2 was administered to rats in sham group, which received sham operations without an ovariectomy, and to rats in the control group.

After administering the test feeds, thigh bones of rats in each experimental group were removed, the amount of bone salts was measured by a bone salt measuring device, and the bone strength was measured by a tension fracture characteristic measuring device.

Results are shown in Table 3 and Table 4.

TABLE 3

| Experimental group | Bone salts (mg, ± SD) |
|---|---|
| Sham group | 120.2 ± 3.9 |
| Control group | 83.5 ± 4.9 |
| Group fed test feed 1 | 104.7 ± 3.6 |
| Group fed test feed 2 | 106.3 ± 4.1 |
| Group fed test feed 3 | 111.3 ± 3.1 |

As shown in Table 3, the amount of bone salts in the thighbone was statistically greater in animals fed the test feeds as compared to those in the control group. Accordingly, it was revealed that sample B and sample C had bone resorption suppressing activity. It was also revealed that the activity was further augmented by the addition of highly absorbable milk-derived calcium.

TABLE 4

| Experimental group | Bone strength (× $10^8$ dyn) |
|---|---|
| Sham group | 13.3 ± 3.6 |
| Control group | 6.7 ± 2.3 |
| Group fed test feed 1 | 10.4 ± 2.9 |
| Group fed test feed 2 | 10.9 ± 2.4 |
| Group fed test feed 3 | 11.9 ± 3.1 |

As shown in Table 4, the bone strength was statistically higher in animals fed the test feeds than in the control animals. Accordingly, it was revealed that sample B and sample C had bone strengthening activity. It was also revealed that the activity was further augmented by the addition of highly absorbable milk-derived calcium.

TEST EXAMPLE 3

Sample B (0.01 mg/100 g) and vitamin D (200 IU) were admixed to an aqueous solution with the basic ingredients shown in Table 5, the admixture was poured into a container and sterilized by heating to produce a drink (test product).

A drink to which albumin (0.01 mg/100 g) was added instead of sample B was prepared in the same manner (control product).

TABLE 5

| Crystalline glucose | 15.0 |
|---|---|
| | (% by weight) |
| Calcium | 0.5 |
| Water | 74.5 |

Sixteen patients having osteoarthritis (shrinkage of joint cleavage) were divided into two groups with 8 patients in each group, and took the abovementioned drinks for one month. The amount of urinary deoxypyridinoline, a bone metabolism marker for bone resorption, was measured before and after the period of drinking. Further, symptoms that patients noticed themselves were confirmed by detailed questioning.

Results are shown in Table 6 and Table 7.

TABLE 6

| | Reduction of deoxypyridinoline (mg, ± SD) |
|---|---|
| Group fed control product | 0.29 ± 0.2 |
| Group fed test product | 0.78 ± 0.2 |

As shown in Table 6, while the amount of deoxypyridinoline was reduced even in the group fed control product with calcium and vitamin, it was reduced further more in the group fed test product. This result revealed that bone resorption due to bone fracture was well suppressed by sample B.

TABLE 7

| | Number of patients showing each symptoms | | | |
|---|---|---|---|---|
| | Group fed control product | | Group fed test product | |
| Symptoms | Before intake | After intake | Before intake | After intake |
| Physically strained joint pain | 8 | 8 | 8 | 5 |
| Joint pain with motion | 6 | 5 | 6 | 3 |
| Joint pain while asleep | 5 | 4 | 5 | 2 |
| Joint pain in exhaustion | 8 | 7 | 8 | 6 |
| Fatigue | 5 | 5 | 4 | 3 |
| Joint pain at the entire cleavage | 6 | 6 | 7 | 6 |

As shown in Table 7, various joint pains were also reduced.

TEST EXAMPLE 4

Golden hamsters (6 weeks of age) were reared normally for one week, after which a sterilized No. 4 silk suture was coiled in five-ply around the M1 column dentis of each animal under ether, and the animals were reared by feeding the feed of Keyes et al. (D#2000: Keyes, P. H. and Jordan: Archs. Oral. Biol., Vol. 9, pp. 377–400, 1964) to induce periodontal disease. The resulting golden hamsters were divided into groups with 18 animals in each group. A test solution was prepared by appropriately diluting each sample A, B or C (10 μg) and applied to the animals of each group 2 times a day every day, keeping the inside of the oral cavity of the animals wet for about 10 minutes each time. Animals in the control group were treated with distilled water. Four weeks after the application, both sides of the lower jawbones were excised after fixed perfusion with a 2.5% glutaraldehyde solution (pH 7.4) for about 20 minutes.

The reduction of alveolar bone mass was evaluated by the following method. Namely, the excised lower bones were fixed with a 2.5% glutaraldehyde solution and soft-X-rayed, and then the resulting photographs were analyzed using an image analyzing device (PIAS LA-555). The area between the enamel cement border and alveolar bone top near M1 was measured to evaluate the reduction in alveolar bone mass.

Results are shown in Table 8.

TABLE 8

| Days after treatment | | Test group A (Sample A) | Test group B (Sample B) | Test group C (Sample C) |
|---|---|---|---|---|
| | Control group | Reduction in area (mm$^2$) | | |
| 5 days | 0.27 | 0.21* | 0.18* | 0.15* |
| 8 days | 0.84 | 0.61* | 0.53* | 0.44* |

*Significantly different from the control group ($p < 0.05$).

As shown in Table 8, reduction in alveolar bone mass in the test groups was significantly low as compared with that in the control group, and the effect was concentration-dependent. Accordingly, it was revealed that the fraction containing a high concentration of milk basic cystatin and its decomposition product were effective in suppressing alveolar bone mass reduction and in preventing periodontal disease.

EXAMPLE 4

The ingredients in Table 9 were mixed, and the mixture was poured into a container and sterilized by heating to produce a drink for the prevention and treatment of various bone diseases such as osteoporosis and bone joint diseases such as rheumatism.

TABLE 9

| Mixed isomerized sugars | 15.00 |
|---|---|
| | (% by weight) |
| Fruit juice | 10.00 |
| Citric acid | 0.50 |

TABLE 9-continued

| | |
|---|---|
| Sample B | 0.01 |
| Flavoring | 0.10 |
| Calcium | 0.50 |
| Vitamin D | (200 IU) |
| Water | 73.89 |

EXAMPLE 5

The ingredients in Table 10 were mixed, and then the mixture was molded under pressure to produce tablets for the prevention and treatment of various bone diseases such as osteoporosis and bone joint diseases such as rheumatism.

TABLE 10

| | |
|---|---|
| Hydrous crystalline glucose | 93.5 |
| | (% by weight) |
| Sample B | 0.1 |
| Calcium | 5.0 |
| Vitamin D | (200 IU) |
| Sugar esters | 1.0 |
| Flavoring | 0.4 |

EXAMPLE 6

The ingredients in Table 11 were mixed, and then the mixture was poured into a container and sterilized by heating to produce jelly for the prevention and treatment of various bone diseases such as osteoporosis and bone joint diseases such as rheumatism.

TABLE 11

| | |
|---|---|
| Fructose | 20.00 |
| | (% by weight) |
| Granulated sugar | 15.00 |
| Starch syrup | 5.00 |
| Agar | 1.00 |
| Sample C | 0.01 |
| Flavoring | 0.10 |
| Calcium | 0.10 |
| Water | 58.79 |

EXAMPLE 7

The ingredients in Table 12 were mixed, and then the admixture was emulsified at an emulsifying temperature of 85C to produce cheese for the prevention and treatment of various bone diseases such as osteoporosis and bone joint diseases such as rheumatism.

TABLE 12

| | |
|---|---|
| Gouda cheese | 43.0 |
| | (% by weight) |
| Cheddar cheese | 43.5 |
| Sodium citrate | 2.0 |
| Sample C | 0.1 |
| Milk-derived calcium | 1.0 |
| Water | 10.4 |

EXAMPLE 8

The ingredients in Table 13 were mixed to produce a dog food for the prevention and treatment of various bone diseases such as osteoporosis and bone joint diseases such as rheumatism.

TABLE 13

| | |
|---|---|
| Soybean cake | 12.0 |
| | (% by weight) |
| Powdered skim milk | 14.0 |
| Soybean oil | 4.0 |
| Corn oil | 2.0 |
| Palm oil | 27.9 |
| Corn starch | 15.0 |
| Flour | 9.0 |
| Bran | 2.0 |
| Vitamin mixture | 9.0 |
| Mineral mixture | 2.0 |
| Cellulose | 3.0 |
| Sample B | 0.1 |

EXAMPLE 9

The ingredients in Table 14 were mixed, and then the mixture was made into a cream and poured into a container to produce a tooth paste for the prevention and treatment of periodontal disease.

TABLE 14

| | |
|---|---|
| Glycerine | 70.49 |
| | (% by weight) |
| Silicon dioxide | 20.00 |
| Xanthan gum | 1.00 |
| Mint flavoring | 1.00 |
| Titanium dioxide | 0.70 |
| Sodium fluoride | 0.30 |
| Distilled water | 6.50 |
| Sample C | 0.01 |

EXAMPLE 10

A column filled with 3 kg of sulfonated Chitopearl (Fuji Boseki, Co., Ltd.), a cation exchange resin, was thoroughly washed with deionized water. Non-pasteurized skimmed milk (300 L) was passed through the column at a flow rate of 100 ml/minute, the column was thoroughly washed with deionized water, and then elution was carried out with a 0.02 M bicarbonate buffer solution containing 0.87 M sodium chloride (pH 6.7) to recover a milk-derived basic protein fraction which was adsorbed onto the resin. The resulting eluate was desalted and concentrated by treating with a reverse osmotic membrane, after which the concentrate was freeze-dried to obtain a powered milk-derived basic protein composition. This procedure was repeated 5 times to obtain 1.65 kg of the milk-derived basic protein composition.

The milk-derived basic protein composition (1 kg) was dissolved at a concentration of 1% by weight in a sodium carbonate buffer solution (pH 9.0) and the solution was passed through a column filled with an anion exchange resin, Q-Sepharose (20 L/hour), and then 100 L of a sodium carbonate buffer solution (pH 9.0) was passed through the column to recover 200 L of a fraction which was not adsorbed onto the resin. Next, this fraction was passed through a column filled with a cation exchange resin, S-Sepharose (20 L/hour), and then the column was washed with 20 L of a sodium carbonate buffer solution (pH 9.0) followed by 15 L of an aqueous 0.5 M sodium chloride solution, after which 10 L of an aqueous 0.5 M sodium chloride solution were passed through the column to obtain 10 L of an eluted fraction. This eluted fraction was concentrated 10 times by treating with an ultrafiltration membrane (UF) (cut-off molecular weight: 10 kDa), the resulting concentrate was desalted by diafiltration (DF) to obtain 1 kg of a concentrated, desalted fraction. This concentrated, desalted fraction was freeze-dried to obtain 74 g of a fraction containing a high concentration of milk basic cystatin. The milk basic cystatin content of this fraction containing a high concentration of milk basic cystatin was 1.6% by weight.

EXAMPLE 11

The fraction containing a high concentration of milk basic cystatin (1 g) obtained in Example 1 was suspended in 100 ml of water, pancreatin was added at a final concentration of 1% by weight to this suspension, and enzyme treatment was carried out at 37C for 5 hours. Then, the enzyme was inactivated by heating at 90C for 5 minutes, after which 0.95 g of the decomposition product of the fraction containing a high concentration of milk basic cystatin was obtained by freeze-drying.

TEST EXAMPLE 5

Splint bones of ICR mice (10–20 days of age) were taken out, soft tissues were removed, then the splint bones were mechanically ground in an $\alpha$-MEM solution containing 5% fetal calf serum to obtain entire bone marrow cells including osteoclasts. These cells (about $2 \times 10^6$) were spotted on an ivory piece using an $\alpha$-MEM solution containing 5% fetal calf serum. After several hours, an $\alpha$-MEM solution containing 5% fetal calf serum, to which each sample was added, was added to the spot, and the ivory piece was incubated for 3 days to examine bone resorption activity of osteoclasts.

After incubation, cells on the ivory piece were pealed, stained with hematoxylin, and subjected to image analysis using PIASLA-555 to count the number of bone resorption pits to evaluate the bone resorption activity.

Thus, a sample solution was each prepared at a concentration of 500 mg/ml for the fraction containing a high concentration of milk basic cystatin obtained in Example 1 (test sample A) and for the fraction containing a high concentration of milk basic cystatin obtained in Example 2 (test sample B) to determine the bone resorption activity. Namely, the bone resorption pits were counted in a culture with an added test sample and compared with the bone resorption pit counts in a culture without an added test sample (referred to as 100%) to express the bone resorption activity. Results are shown in Table 15.

TABLE 15

| | Bone resorption activity (%, ± SD) |
|---|---|
| Test sample A | 70.9 ± 4.1 |
| Test sample B | 60.6 ± 2.9 |

As shown in Table 15, the fraction containing a high concentration of milk basic cystatin and the decomposition product of the fraction containing a high concentration of milk basic cystatin were revealed to be effective in suppressing bone resorption activity.

TEST EXAMPLE 6

An animal experiment was carried out using osteoporosis model rats for test sample A obtained in Example 10 and test sample B obtained in Example 11.

Basic ingredients of the feed administered to the rats are shown in Table 2. The amount of both calcium and phosphorus was 300 mg per 100 g feed in all test groups so that the calcium to phosphorus ratio was 1:1.

TABLE 16

| Sucrose | 50.0 |
|---|---|
| | (% by weight) |
| Casein | 20.0 |
| Cornstarch | 15.0 |
| Cellulose | 5.0 |
| Corn oil | 5.0 |
| Vitamin mixture (including choline) | 1.0 |
| Mineral mixture | 4.0[1)] |

[1)]Calcium carbonate was admixed as a calcium source.

The following test feeds were prepared by adding test sample A or B to the feed with the basic ingredients shown in Table 16.

Test feed 1: Feed with the basic ingredients in Table 16+Test sample A (0.05 mg/100 g)

Test feed 2: Feed with the basic ingredients in Table 16+Test sample B (0.05 mg/100 g)

Test feed 3: Feed with the basic ingredients in Table 16 (except that milk-derived calcium (Japanese Patent Application Laid-open H4-306622) was used as a calcium source instead of calcium carbonate)+Test sample A (0.05 mg/100 g)

Female SD female rats (40 weeks of age) were used for experimental animals. After preliminary rearing for one week, an ovariectomy was performed, and then the rats were reared further for 2 weeks on a low calcium diet to create osteoporosis model rats. Sham operations without an ovariectomy were performed to create sham rats. The rats were divided into groups, 7 rats in one group, and fed the test feeds for one month. The feed with the basic ingredients shown in Table 16 was administered to rats in sham group, and to rats in the control group.

After administering the test feeds, thigh bones of rats in each experimental group were removed, the amount of bone salts was measured by a bone salt measuring device, and the bone strength was measured by a tension fracture characteristic measuring device. Results are shown in Table 17 and Table 18.

TABLE 17

| Experimental group | Bone salts (mg, ± SD) |
|---|---|
| Sham group | 138.2 ± 3.6 |
| Control group | 89.1 ± 3.2 |
| Group fed test feed 1 | 101.2 ± 3.9 |
| Group fed test feed 2 | 113.3 ± 3.1 |
| Group fed test feed 3 | 110.1 ± 3.5 |

As shown in Table 17, the amount of bone salts in the thighbone was statistically greater in animals fed the test feeds as compared to those in the control group. Accordingly, it was revealed that sample A and sample B had bone resorption suppressing activity. It was also revealed that the activity was further augmented by the addition of highly absorbable milk-derived calcium.

TABLE 18

| Experimental group | Bone strength (× $10^8$ dyn) |
| --- | --- |
| Sham group | 13.4 ± 2.3 |
| Control group | 6.5 ± 2.1 |
| Group fed test feed 1 | 8.6 ± 2.2 |
| Group fed test feed 2 | 11.1 ± 2.0 |
| Group fed test feed 3 | 10.5 ± 2.4 |

As shown in Table 18, the bone strength was statistically higher in animals fed the test feeds than in the control animals. Accordingly, it was revealed that sample A and sample B had bone strengthening activity. It was also revealed that the activity was further augmented by the addition of highly absorbable milk-derived calcium.

Sample A (0.05 mg/100 g) and vitamin D (200 IU) were admixed to an aqueous solution with the basic ingredients shown in Table 19, the admixture was poured into a container and sterilized by heating to produce a drink (test product).

A drink to which albumin (0.05 mg/100 g) was added instead of sample A was prepared in the same manner (control product).

TABLE 19

| Crystalline glucose | 15.0 |
| --- | --- |
|  | (% by weight) |
| Calcium | 0.5 |
| Water | 74.5 |

20 patients having osteoarthritis (shrinkage of joint cleavage) were divided into two groups with 10 patients in each group, and took the abovementioned drinks for one month. The amount of urinary deoxypyridinoline, a bone metabolism marker for bone resorption, was measured before and after the period of drinking. Further, symptoms that patients noticed themselves were confirmed by detailed questioning.

Results are shown in Table 20 and Table 21.

TABLE 20

| | Reduction of deoxypyridinoline (mg, ± SD) |
| --- | --- |
| Group fed control product | 0.25 ± 0.2 |
| Group fed test product | 0.56 ± 0.2 |

As shown in Table 20, while the amount of deoxypyridinoline was reduced even in the group fed control product with calcium and vitamin, it was reduced further more in the group fed test product. This result revealed that bone resorption due to bone fracture was well suppressed by sample A.

TABLE 21

| | Number of patients showing each symptom | | | |
| --- | --- | --- | --- | --- |
| | Group fed control product | | Group fed test product | |
| Symptoms | Before intake | After intake | Before intake | After intake |
| Physically strained joint pain | 10 | 10 | 10 | 6 |
| Joint pain with motion | 6 | 5 | 5 | 2 |
| Joint pain while asleep | 5 | 6 | 5 | 1 |
| Joint pain in exhaustion | 9 | 8 | 8 | 4 |
| Fatigue | 6 | 5 | 7 | 5 |
| Joint pain at the entire cleavage | 9 | 8 | 9 | 6 |

As shown in Table 21, various joint pains were also reduced.

TEST EXAMPLE 8

Golden hamsters (6 weeks of age) were reared normally for one week, after which a sterilized No. 4 silk suture was coiled in five-ply around the M1 column dentis of each animal under ether, and the animals were reared by feeding the feed of Keyes et al. (D#2000: Keyes, P. H. and Jordan: Archs. Oral. Biol., Vol. 9, pp. 377–400, 1964) to induce periodontal disease. The resulting golden hamsters were divided into groups with 18 animals in each group. A test solution was prepared by appropriately diluting each sample A or B (50 μg) and applied to the animals of each group 2 times a day every day, keeping the inside of the oral cavity of the animals wet for about 10 minutes each time. Animals in the control group were treated with distilled water. Four weeks after the application, both sides of the lower jawbones were excised after fixed perfusion with a 2.5% glutaraldehyde solution (pH 7.4) for about 20 minutes.

The reduction of alveolar bone mass was evaluated by the following method. Namely, the excised lower bones were fixed with a 2.5% glutaraldehyde solution and soft-X-rayed, and then the resulting photographs were analyzed using an image analyzing device (PIAS LA-555). The area between the enamel cement border and alveolar bone top near M1 was measured to evaluate the reduction in alveolar bone mass.

Results are shown in Table 22.

TABLE 22

| Days after treatment | Control group | Test group A (Sample A) Reduction in area (mm²) | Test group B (Sample B) |
|---|---|---|---|
| 4 days | 0.32 | 0.25* | 0.21* |
| 9 days | 0.89 | 0.65* | 0.53* |

*Significantly different from the control group ($p < 0.05$).

As shown in Table 22, reduction in alveolar bone mass in the test groups was significantly low as compared with that in the control group, and the effect was concentration-dependent. Accordingly, it was revealed that the fraction containing a high concentration of milk basic cystatin and its decomposition product were effective in suppressing alveolar bone mass reduction and in preventing periodontal disease.

EXAMPLE 12

The ingredients in Table 23 were mixed, and then the resulting dough was molded and baked to produce biscuits for the prevention and treatment of various bone diseases such as osteoporosis and bone joint diseases such as rheumatism.

TABLE 23

| Flour | 50.0 |
|---|---|
|  | (% by weight) |
| Sugar | 20.0 |
| Table salt | 0.5 |
| Margarine | 12.5 |
| Egg | 12.1 |
| Water | 4.0 |
| Sodium hydrogencarbonate | 0.1 |
| Ammonium bicarbonate | 0.2 |
| Calcium carbonate | 0.5 |
| Test sample A | 0.1 |

EXAMPLE 13

The ingredients in Table 24 were mixed, and then the mixture was poured into a container and sterilized by heating to produce jelly for the prevention and treatment of various bone diseases such as osteoporosis and bone joint diseases such as rheumatism.

TABLE 24

| Fructose | 20.00 |
|---|---|
|  | (% by weight) |
| Granulated sugar | 15.00 |
| Starch syrup | 5.00 |
| Agar | 1.00 |
| Sample B | 0.01 |
| Flavoring | 0.10 |
| Calcium Carbonate | 0.10 |
| Water | 58.79 |

EXAMPLE 14

The ingredients in Table 25 were mixed, and then the admixture was emulsified at an emulsifying temperature of 85C to produce cheese for the prevention and treatment of various bone diseases such as osteoporosis and bone joint diseases such as rheumatism.

TABLE 25

| Gouda cheese | 43.0 |
|---|---|
|  | (% by weight) |
| Cheddar cheese | 43.5 |
| Sodium citrate | 2.0 |
| Sample B | 0.1 |
| Milk-derived calcium | 1.0 |
| Water | 10.4 |

EXAMPLE 15

Skim milk (12%) was pasteurized by heating at 90C for 20 minutes, and *Lactobacillus acidophilus* or *Streptococcus thermophilus* was individually inoculated to make two kinds of starter cultures. The ingredients in Table 12 including a yogurt mix, whose major component is milk, were mixed, and then the admixture was subjected to conventional fermentation and cooling to produce yogurt for the prevention and treatment of various bone diseases such as osteoporosis and bone joint diseases such as rheumatism.

TABLE 26

| Yogurt mix | 96.99 |
|---|---|
|  | (% by weight) |
| *L. acidophilus* | 1.50 |
| *S. thermophilus* | 1.50 |
| Test sample A | 0.01 |

EXAMPLE 16

The ingredients in Table 27 were mixed, and then the mixture was molded under pressure to produce tablets for the prevention and treatment of various bone diseases such as osteoporosis and bone joint diseases such as rheumatism.

TABLE 27

| Hydrous crystalline glucose | 93.5 |
|---|---|
|  | (% by weight) |
| Sample A | 0.05 |
| Calcium | 5.0 |
| Vitamin D | (200 IU) |
| Sugar esters | 1.0 |
| Flavoring | 0.4 |

EXAMPLE 17

The ingredients in Table 28 were mixed to produce a dog food for the prevention and treatment of various bone diseases such as osteoporosis and bone joint diseases such as rheumatism.

TABLE 28

| Soybean cake | 12.0 |
|---|---|
|  | (% by weight) |
| Powdered skim milk | 14.0 |
| Soybean oil | 4.0 |
| Corn oil | 2.0 |
| Palm oil | 27.9 |
| Corn starch | 15.0 |
| Flour | 9.0 |
| Bran | 2.0 |
| Vitamin mixture | 9.0 |
| Mineral mixture | 2.0 |

TABLE 28-continued

| | |
|---|---|
| Cellulose | 3.0 |
| Sample A | 0.1 |

EXAMPLE 18

The ingredients in Table 29 were mixed, and then the mixture was made into a cream and poured into a container to produce a tooth paste for the prevention and treatment of periodontal disease.

TABLE 29

| | |
|---|---|
| Glycerine | 70.49 |
| | (% by weight) |
| Silicon dioxide | 20.00 |
| Xanthan gum | 1.00 |
| Mint flavoring | 1.00 |
| Titanium dioxide | 0.70 |
| Sodium fluoride | 0.30 |
| Distilled water | 6.50 |
| Sample B | 0.01 |

Effectiveness of the Invention

Since a fraction containing a high concentration of milk basic cystatin and a decomposition product produced by decomposing this fraction containing a high concentration of milk basic cystatin with a protease, both obtained according to the present invention, have a bone formation stimulating and bone resorption suppressing activities, they can be effectively used for the prevention and treatment of various bone diseases such as osteoporosis, bone joint diseases such as rheumatism, and periodontal disease by admixing them into a drink, food product, medicine, feed, or the like.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for producing a fraction containing milk basic cystatin or its decomposition product, comprising the steps of: (i) preparing a composition containing a basic protein fraction from milk; (ii) contacting said composition with a heparin-immobilized resin; (iii) eluting a fraction from the resin; (iv) subjecting said fraction to ultrafiltration using a membrane having a cut-off molecular weight of 10–50 kDa; (v) recovering a permeate from said ultrafiltration membrane to obtain a fraction containing milk basic cystatin, wherein said fraction has inhibitory activity on proteolytic activity of cysteine proteases and on virus growth; and optionally (vi) decomposing the permeate with a protease to obtain a decomposition product, wherein said protease is selected from the group consisting of trypsin, chymotrypsin, pepsin, papain, kallikrein, cathepsin, thermolysin, and V8 protease, and wherein the decomposition product has a bone resorption suppressing activity.

2. The method as claimed in claim 1, wherein the step of preparing said composition containing the basic protein from milk comprises the steps of: providing a protein fraction from milk; heating the protein fraction from milk to precipitate a first precipitate; recovering a supernatant by removing the first precipitate; precipitating a second precipitate by adding alcohol to said supernatant; and recovering a supernatant by removing the second precipitate.

3. The method as claimed in claim 2, wherein the heating of the protein fraction from milk is conducted at from 80° C. to 90° C.

4. The method as claimed in claim 2, wherein an amount of the alcohol is added such that the final concentration of the alcohol prior to the recovery is from 70% to 80%.

5. The method as claimed in claim 2, wherein said protein fraction from milk is obtained by the steps of: providing a milk; contacting the milk with a cation-exchange resin; and eluting a fraction from the resin to recover said protein fraction.

6. The method as claimed in claim 5, further comprising a step of desalting said recovered fraction.

7. The method as claimed in claim 1, wherein the fraction containing milk basic cystatin contains 1% or higher milk basic cystatin by dry weight.

8. A method for producing a fraction containing milk basic cystatin or its decomposition product, comprising the steps of: (i) preparing a basic protein composition from milk; (ii) contacting said basic protein composition from milk with an anion exchange resin; (iii) eluting a fraction from said resin; (iv) contacting said fraction with a cation exchange resin; (v) eluting from said resin to recover a fraction containing milk basic cystatin, wherein said fraction has inhibitory activity on proteolytic activity of cysteine proteases and on virus growth; and optionally (vi) decomposing the recovered fraction with a protease to obtain a decomposition product, wherein said protease is selected from the group consisting of trypsin, chymotrypsin, pepsin, papain, kallikrein, cathepsin, thermolysin, and V8 protease, and wherein the decomposition product has a bone resorption suppressing activity.

9. The method as claimed in claim 8, wherein said basic protein composition from milk is obtained by the steps of: providing a milk; contacting the milk with a cation exchange resin; and eluting a fraction from said resin.

10. The method as claimed in claim 9, further comprising a step of desalting said recovered fraction.

11. The method as claimed in claim 8, wherein the fraction containing milk basic cystatin contains 1% or higher milk basic cystatin by dry weight.

12. A drink or food product comprising a fraction containing milk basic cystatin or its decomposition product obtained by the method of claim 1.

13. The drink or food product as claimed in claim 12, wherein the milk basic cystatin or its decomposition product in the fraction is in an amount of 1 µg–100 mg/100 g.

14. The drink or food product as claimed in claim 12, which further contain at least one of calcium or vitamins.

15. A medicament for the treatment or osteoporosis, bone joint disease, and periodontal disease, which comprises a fraction containing milk basic cystatin or its decomposition product obtained by the method of claim 1, wherein the milk basic cystatin or its decomposition product in the fraction is in an amount of 1 µg–100 mg/100 g.

16. The medicament as claimed in claim 15, which further contains at least one of calcium or vitamins.

17. A feed comprising a fraction containing milk basic cystatin or its decomposition product obtained by the method of claim 1.

18. The feed as claimed in claim 17, wherein the milk basic cystatin or its decomposition product in the fraction is in an amount of 1 µg–100 mg/100 g.

19. The feed as claimed in claim 17, which further contains at least one of calcium or vitamins.

20. A drink or food product comprising a fraction containing milk basic cystatin or its decomposition product obtained by the method of claim 8.

21. The drink or food product as claimed in claim 20, wherein the milk basic cystatin or its decomposition product in the fraction is in an amount 50 µg–500 mg/100 g.

22. The drink or food product as claimed in claim 20, which further contains at least one of calcium or vitamins.

23. A medicament for the treatment of osteoporosis, bone joint disease, and periodontal disease, which comprises a fraction containing milk basic cystatin or its decomposition product obtained by the method of claim 8, wherein the milk basic cystatin or its decomposition product in the fraction is in an amount of 5 µg–500 mg/100 g.

24. The medicament as claimed in claim 23, which further contains at least one of calcium or vitamins.

25. A feed comprising a fraction containing milk basic cystatin or its decomposition product obtained by the method of claim 8.

26. The feed as claimed in claim 25, wherein the milk basic cystatin or its decomposition product in the fraction is in an amount of 5 µg–500 mg/100 g.

27. The feed as claimed in claim 25, which further contains at least one of calcium or vitamins.

* * * * *